United States Patent [19]

Gonzalez y. Rojas

[11] 4,183,579
[45] Jan. 15, 1980

[54] DOCTOR'S STOOL

[76] Inventor: Enrique M. Gonzalez y. Rojas, Buenaventura #383-2, Ft. Chapultepec, Apartado Postal 954, Tijuana, Baja California, Mexico

[21] Appl. No.: 905,799

[22] Filed: May 15, 1978

[51] Int. Cl.² .............................................. B62J 1/00
[52] U.S. Cl. ................... 297/195; 248/171; 297/310
[58] Field of Search ............... 297/195, 310, 208, 209; 248/169, 170, 171, 131, 158, 160, 161, 415, 188.9

[56] References Cited

U.S. PATENT DOCUMENTS

| | | | |
|---|---|---|---|
| 659,089 | 10/1900 | McKinney | 248/160 |
| 900,077 | 10/1908 | Barnickle | 297/310 |
| 912,310 | 2/1909 | Barnickle | 297/310 |
| 2,402,934 | 6/1946 | Wood | 248/161 |
| 2,812,614 | 11/1957 | Ladyman | 248/188.9 |
| 3,203,657 | 8/1965 | Thompson | 248/171 |
| 3,282,530 | 11/1966 | Rash | 248/170 X |
| 3,371,959 | 3/1968 | Gordin | 297/310 |
| 3,926,472 | 12/1975 | Evans | 297/310 |

FOREIGN PATENT DOCUMENTS 336216  3/1920  Fed. Rep. of Germany ........... 297/195

Primary Examiner—Roy D. Frazier
Assistant Examiner—Peter A. Aschenbrenner
Attorney, Agent, or Firm—Brown & Martin

[57] ABSTRACT

A stool type seat having a base with floor engaging suction cups to hold the stool in place, the single supporting post having a spring centered hinge to allow the post to tilt in any direction. A saddle type seat is rotatably mounted on top of the post. Stabilizing legs are attached to the post and are hinged to allow the post to swing forward and to some extent to either side, but the legs lock when the post is upright to prevent the stool from tipping over backwards. The structure folds and breaks down into compact components for transportation and storage.

4 Claims, 5 Drawing Figures

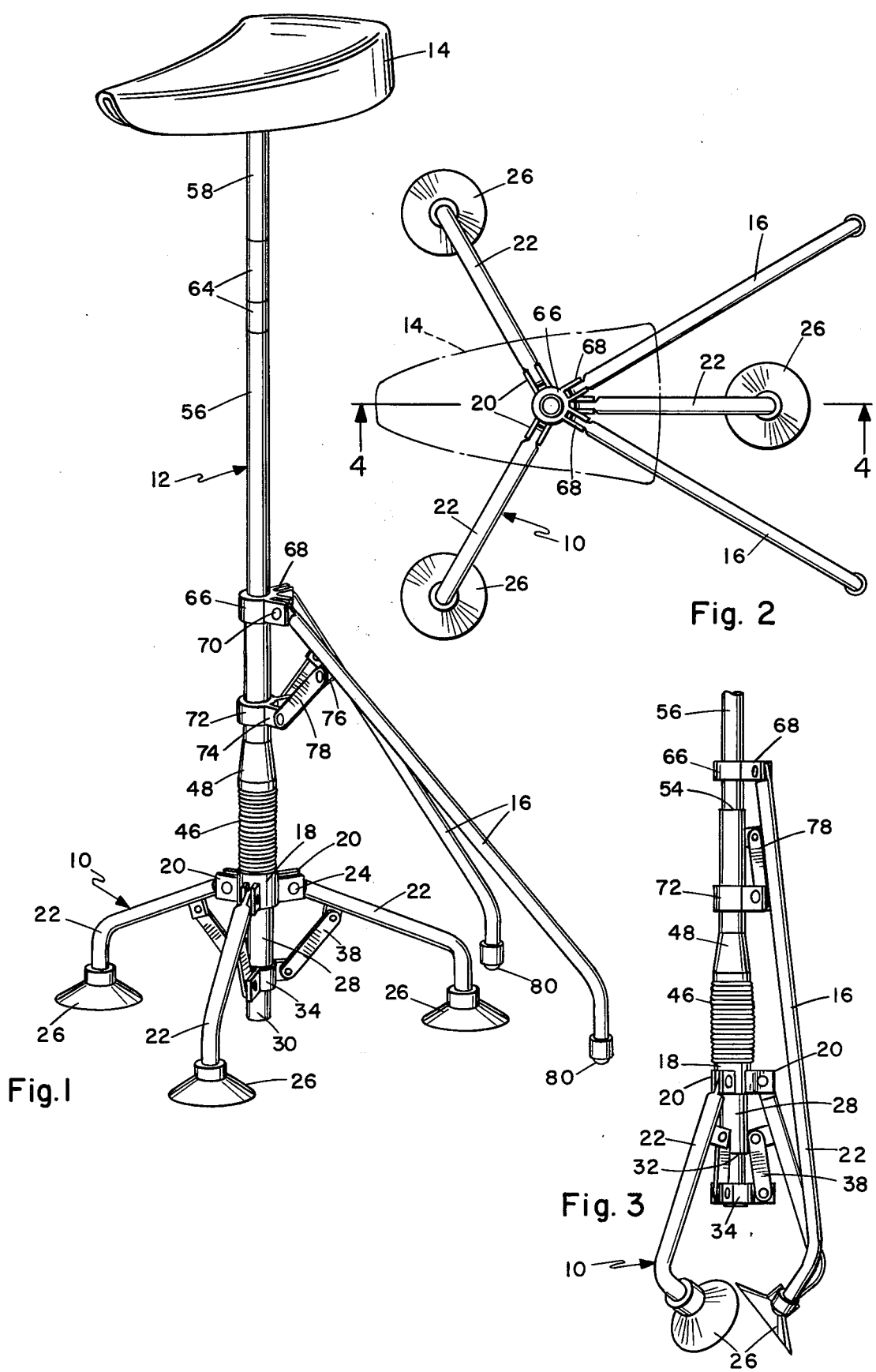

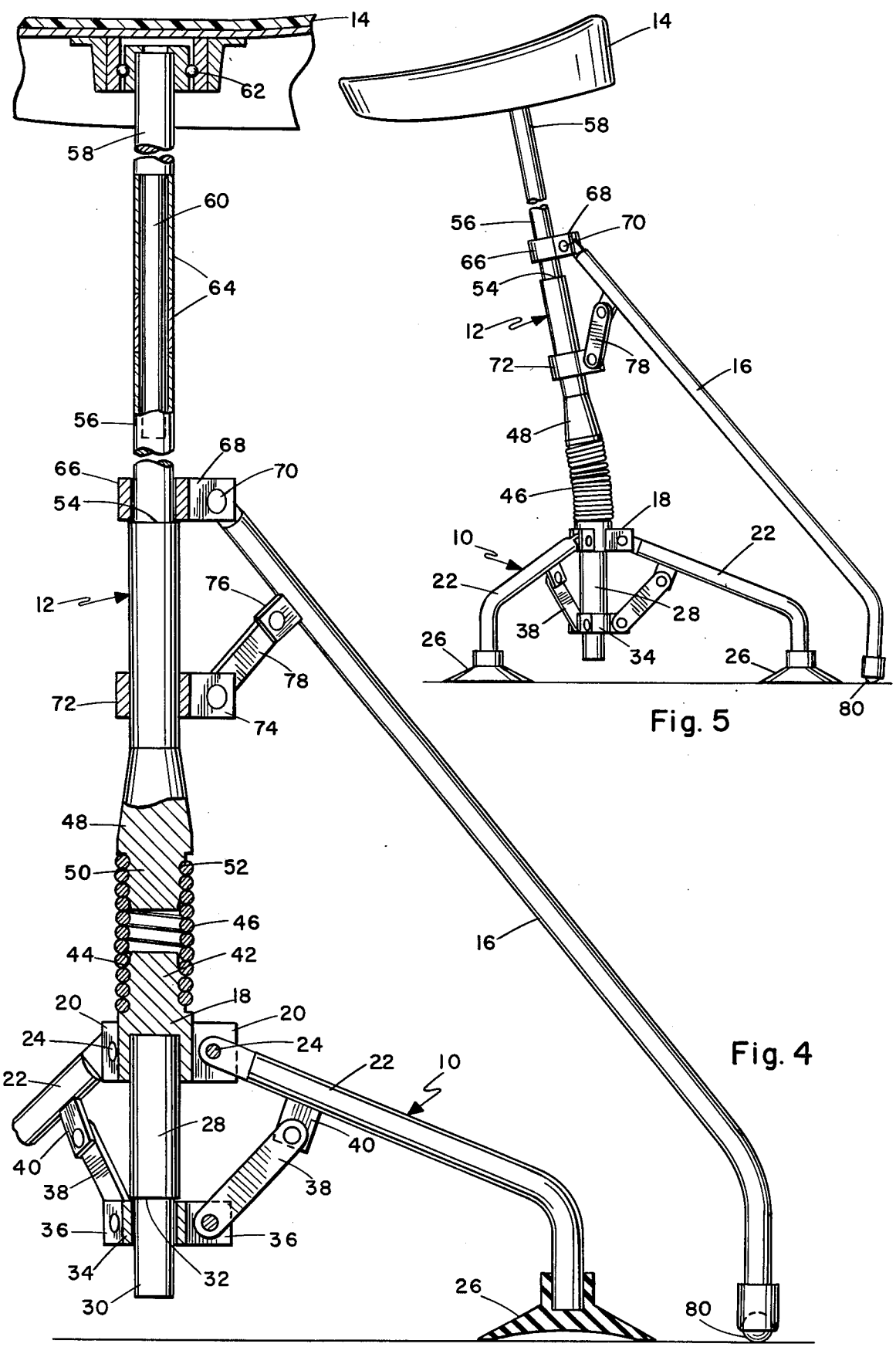

DOCTOR'S STOOL

BACKGROUND OF THE INVENTION

Some surgical procedures are lengthy and a doctor must often stand for several hours, almost in the same position. Without some means for resting the procedure can be very tiring and may affect the doctor's performance.

At a conventional operating table a high chair or stool is necessary for the doctor to maintain a standing or near standing position. However, a conventional stool can obstruct the doctor's movements and must be moved frequently. If the stool is on wheels or rollers, it can slip out of position at a crucial moment and upset the doctor's balance. It would be very desirable to have a stool on which the doctor could remain seated to minimize fatigue, yet which would accommodate movements of the doctor around the operating position without slipping out of place, or becoming insecure at any time.

SUMMARY OF THE INVENTION

The stool described herein has a single supporting post which is hinged to swing in any direction and is spring biased to the upright position. A tripod type base has floor engaging suction cups which anchor the stool to the floor to prevent sliding. On top of the post is a saddle type seat rotatably mounted for maximum freedom of movement. A doctor using the seat can thus lean forward or to the side while remaining supported on the seat.

To prevent the seat from tipping over backwards when the doctor sits up or leans back slightly to relax, a pair of stabilizing legs is attached to the post to lock in place and hold the post upright under a rearward load. The stabilizing legs are connected to the post by hinged links and the lower ends have rollers which roll on the floor. When the post is tilted forward of the vertical, the stabilizing legs hinge and roll on the floor to follow the post. As the post moves back to the upright position, the legs roll back and then lock when the post is vertical.

In addition to the tilting and the rotatable seat, the stool is also adjustable in height to suit the individual. While the stool is particularly suitable for use by a doctor in surgery, it could also be used by a dentist, or by anyone restricted to a small work area for long periods, to provide support with freedom of movement and security against falling.

The primary object of this invention, therefore, is to provide a new and improved doctor's stool.

Another object of this invention is to provide a doctor's stool which supports the occupant securely while allowing considerable freedom of movement to lean forward and to the sides.

Another object of this invention is to provide a doctor's stool which is stable on the floor and will not tip over backwards.

A further object of this invention is to provide a doctor's stool which is easily dismantled when not in use.

Other objects and advantages will be apparent in the following detailed description, taken in conjunction with the accompanying drawings, in which:

FIG. 1 is a perspective view of the complete doctor's stool.

FIG. 2 is a top plan view of the structure with the seat shown in phantom.

FIG. 3 is a side elevation view of the lower portion of the stool with the legs and base folded.

FIG. 4 is an enlarged sectional view taken on line 4—4 of FIG. 2.

FIG. 5 is a side elevation view of the stool showing the forward tilting action.

DESCRIPTION OF THE PREFERRED EMBODIMENT

The stool comprises, basically, a base 10, a post 12, a seat 14 and a pair of stabilizer legs 16.

Base 10 has a cylindrical hub 18 with three equally spaced radially projecting forks 20. Connected to each fork 20 is a base leg 22, pivotally held by a hinge pin 24 to swing vertically relative to the hub. At the outer end of each base leg 22 is a floor engaging suction cup 26.

Extending axially downwardly from hub 18 is a guide pin 28 having a reduced diameter lower end 30, which defines a shoulder 32 on the pin. Slidably mounted on lower end 30 is a connecting sleeve 34 having three equally spaced radially extending lugs 36. Each base leg 22 is pivotally attached to one fork 36 by a link 38 between lug 36 and a lug 40 on the leg. The base legs 22 can thus be folded downwardly, as in FIG. 3, the connecting sleeve 34 sliding on lower end 30 and equalizing the folding. When the base legs are opened, the connecting sleeve slides up until it engages shoulder 32 and limits the spread of the base legs, as in FIG. 4.

Projecting axially upward from hub 18 is a cylindrical plug 42, having an external helical groove 44 to receive the lower end of a stiff coil spring 46, which is threaded on to the plug. The lower end of post 12 has an enlarged boss 48 with a downwardly projecting plug 50. The plug 50 also has an external helical groove 52, and is threaded into the upper end of spring 46, leaving a small gap between the two plugs, as in FIG. 4.

Post 12 has a shoulder 54 spaced above boss 48, and a reduced diameter tubular stem 56 forming the central portion of the post. The upper post portion 58 has a reduced diameter support pin 60 which is telescopically slidable in stem 56. On the upper end of upper portion 58 is a bearing 62, on which seat 14 is rotatably mounted. The seat as illustrated is a bicycle type saddle for comfortable support with minimum size, and to hold the occupant against slipping. To adjust the height of the seat, tubular spacers 64 of various lengths are placed on support pin 60 between the upper portion 58 and stem 56.

Vertically slidably mounted on stem 56 is a sleeve 66 having a pair of radially extending forks 68, spaced approximately 60 degrees apart. The upper ends of the stabilizer legs 16 are secured in the forks 68 by hinge pins 70. Fixed on post 12 just above the boss 48 is a collar 72 having a pair of radially extending lugs 74, corresponding to forks 68. Each stabilizer leg 16 has a lug 76, from which a link 78 pivotally connects the leg to a lug 74. The lower end of each stabilizer leg 16 has a roller 80 to roll easily on the floor, the stabilizer legs extending well beyond the base legs 22. The preferred alignment is illustrated in FIG. 2, with two base legs 22 extending forwardly and the third base leg extending rearwardly between stabilizer legs 16, in a very well braced configuration.

In use the stool is placed on the floor with the stabilizer legs extending rearwardly from the work position. When the occupant of the stool leans forward, the post 12 tilts by bending spring 46, as in FIG. 5. The stabilizer legs 16 are pulled forward and pivot on hinge pins 70, the sleeve 66 sliding up stem 56 to accommodate the change in position. Links 78 hold the legs in symmetrical alignment. The seat can be tilted forward and also to either side, allowing the occupant considerable freedom while maintaining the support of the seat. When the occupant straightens up, the post returns to the upright position and the stabilizer legs roll back. This causes sleeve 66 to slide down until it rests on shoulder 54, which locks the stabilizer legs in place and braces the post 12 against backward tilting. The stool is thus prevented from tipping over backwards, the tripod base 10 and stabilizer legs 16 providing a very stable support.

The hinged stabilizer legs, which are pulled in close to the base when the seat is tilted forward, are preferred over any type of fixed braces. Fixed stabilizer legs would swing up and out behind the stool and would be a hazard to other personnel in the area.

For storage the stool is easily dismantled by removing seat 14 and the upper post portion 58. Base legs 22 and stabilizer legs 16 can then be folded down below the post structure, as in FIG. 3.

When used in surgery the stool has been found to provide comfortable support for extended periods of time and does not obstruct the movements of the surgeon. The security in knowing that the stool will not tip over backwards allows the surgeon to concentrate on the operating procedures. While the stool is particularly suited for use by a doctor performing surgery, it will be obvious that there are many other uses for such a seat.

Having described my invention, I claim:

1. A stool, comprising:
    a base having spaced floor engaging base legs;
    a post extending upwardly from said base and having a self-centering resilient hinge connection to the base;
    a seat mounted on the upper end of said post;
    a sleeve slidably mounted on said post above said hinge connection;
    a pair of spaced stabilizer legs with upper ends pivotally attached to said sleeve and having floor engaging lower ends extending outwardly beyond the base legs;
    a collar fixed on said post below said sleeve, with links pivotally connecting said stabilizer legs to the collar;
    and a shoulder on said post defining a stop for limiting downward sliding motion of the sleeve and thereby limiting the outward spread of the stabilizer legs.

2. A stool according to claim 1, wherein said stabilizer legs have floor engaging rollers in the lower ends thereof.

3. A stool according to claim 1, wherein said base has a central hub with a pair of said base legs extending forwardly and a third base leg extending rearwardly therefrom;
    said stabilizer legs extending rearwardly on opposite sides of said third leg.

4. A stool according to claim 3, wherein said base legs are pivotally attached to said hub to fold downwardly therefrom;
    said hub having a downwardly projecting guide pin, a connecting sleeve axially slidable on said guide pin, and links pivotally connecting said base legs to said sleeve;
    said guide pin having a shoulder comprising a stop for limiting the upward sliding motion of the connecting sleeve.

* * * * *